United States Patent
Tikkanen (10) Patent No.: US 8,710,849 B2
(45) Date of Patent: Apr. 29, 2014

(54) PARTICLE MEASUREMENT PROCESS AND APPARATUS

(75) Inventor: Juha Tikkanen, Tampere (FI)

(73) Assignee: Pegasor Oy, Tampere (FI)

( * ) Notice: Subject to any disclaimer, the term of this patent is extended or adjusted under 35 U.S.C. 154(b) by 322 days.

(21) Appl. No.: 12/920,361

(22) PCT Filed: Mar. 4, 2009

(86) PCT No.: PCT/FI2009/000031
§ 371 (c)(1),
(2), (4) Date: Aug. 31, 2010

(87) PCT Pub. No.: WO2009/109688
PCT Pub. Date: Sep. 11, 2009

(65) Prior Publication Data
US 2011/0050243 A1    Mar. 3, 2011

(30) Foreign Application Priority Data

Mar. 4, 2008 (FI) .................................. 20080182

(51) Int. Cl.
*G01N 27/62* (2006.01)
*H02N 3/00* (2006.01)
*H01J 49/00* (2006.01)

(52) U.S. Cl.
USPC ............. 324/464; 324/468; 324/459; 310/10; 250/288

(58) Field of Classification Search
USPC ....................................................... 324/464
See application file for complete search history.

(56) References Cited

U.S. PATENT DOCUMENTS

| | | | | |
|---|---|---|---|---|
| 3,518,461 A | * | 6/1970 | Marks ............................. | 310/10 |
| 4,008,620 A | * | 2/1977 | Narato et al. .............. | 73/864.34 |
| 4,069,665 A | * | 1/1978 | Bolasny .......................... | 60/275 |
| 4,631,482 A | * | 12/1986 | Newton et al. ................ | 324/454 |
| 5,528,150 A | * | 6/1996 | Stearns et al. ................ | 324/464 |
| 2006/0284077 A1 | * | 12/2006 | Fissan et al. .................. | 250/288 |

FOREIGN PATENT DOCUMENTS

| | | |
|---|---|---|
| DE | 4008348 A1 | 9/1991 |
| JP | 60209167 A | 10/1985 |
| JP | 2006153746 A | 6/2006 |
| JP | 2006250576 A | 9/2006 |
| WO | WO-2004113904 A1 | 12/2004 |

OTHER PUBLICATIONS

International Search Report and Written Opinion for corresponding International Application No. PCT/FI2009/000031, dated Jul. 14, 2009.
Romay et al., A sonic jet corona ionizer for electrostatic discharge and aerosol neutralization, Aerosol Sci. Technol., 20(1):31-41 (1994).
Supplementary European Search Report for corresponding European application No. EP 09718494, dated Mar. 27, 2012.
Office Action in Japanese and English, Japanese Patent Application No. 2010-549166, mailing date May 24, 2013.

* cited by examiner

*Primary Examiner* — Jermele M Hollington
*Assistant Examiner* — Christopher McAndrew
(74) *Attorney, Agent, or Firm* — Marshall, Gerstein & Borun LLP (57) ABSTRACT

A process for measuring particle concentrations in a gas using an ejector for producing an essentially constant sample flow and for efficient mixing of the particle-containing sample and essentially clean, ionized gas. The invention also relates to an apparatus implementing such process. The process and the apparatus can be utilized for example in measuring particle concentrations in an exhaust system of a combustion engine.

24 Claims, 5 Drawing Sheets

PARTICLE MEASUREMENT PROCESS AND APPARATUS

CROSS-REFERENCE TO RELATED APPLICATIONS

This is the U.S. national phase of International Application No. PCT/FI2009/000031, filed Mar. 4, 2009, which claims the benefit of Finnish Patent Application No. 20080182, filed Mar. 4, 2008.

BACKGROUND OF THE INVENTION

1. Field of Invention

The invention relates to a process for measuring particle concentrations in an aerosol. The invention also relates to an apparatus that implements that process. The process and the apparatus can be utilized for example in measuring particle concentrations in an exhaust system of a combustion engine.

2. Description of the State of the Art

For various reasons, it is important to be able to measure fine particles, especially the ones born in combustion engines. The measurement activities are driven by increasing concern about the potential health effects of fine particles, and these health concerns have led to limits being imposed on fine particle emissions. In the future, these limits on particle emissions will continuously become tighter. Another need for fine particle measurements arises from the development of combustion engines and from real-time monitoring of combustion engines, especially diesel engines. Still another need for fine particle measurements arises from the increasing production and use of nano-sized particles in industrial processes, the particles typically having a diameter of less than 100 nm. Both the monitoring of these industrial processes and occupational health and safety issues require reliable fine particle measurement.

Diesel engines exhaust particles in three different size ranges: nuclei-sized particles have a diameter of less than approximately 50 nm, accumulation-sized particles have diameters between 50 nm and 1 .mu.m, and coarse-sized particles have a diameter of greater than 1 .mu.m. A majority of the diesel engine exhaust particles are created after the exhaust gases escape from the exhaust pipe and these particles typically are nuclei-sized.

A particle trap is typically installed to the exhaust pipe of a combustion engine to keep the fine particle concentrations below the exhaust limits. The trap requires frequent regeneration and the trapped particles are combusted by increasing the temperature of the trap and simultaneously feeding excess air to the trap, so that the carbon containing particles are burnt.

The patent publication F1 118278 B, Dekati Oy, 25 Dec. 2004, relates to a method and a sensor device for determining particle emissions from exhaust gases of a combustion engine substantially during the use in an exhaust pipe system or a corresponding exhaust gas duct, in which method emitted particles contained in the exhaust gases are charged and the particle emissions are determined by measuring the electric charge carried by the emitted particles in said exhaust gas duct. According to the invention, the emitted particles are charged by varying the way of charging or the charging power over time in such a manner that, as a result of said charging, emitted particles brought into at least two different electrical charge states are present, wherein the charge of the emitted particles is further determined as a difference value/values measured from the emitted particles brought into said at least two different electrical charge states. The problem with the described method is that the particles are charged by a charger placed inside the exhaust gas duct, where the charger is easily soiled, shortening the lifespan and reliability of the charger. Varying particle concentration and constant ion generation cause problems in maintaining constant particle charging. The formation of fine particles in the exhaust duct is a complicated process and making measurements in an environment with a greatly varying mass flow is very difficult. Different fuels and different lubricants affect the particle concentrations and particle properties in the exhaust gas duct, as described e.g. in Heejung Jung, et al., The Influence of Engine Lubricating Oil on Diesel Nanoparticle Emissions and Kinetics of Oxidation, SAE International 2003-01-3179, 2003.

The publication of Francisco J. Romay, et al., A Sonic Jet Corona Ionizer for Electrostatic Discharge and Aerosol Neutralization, Aerosol Science and Technology, Vol. 20 (1994), pp. 31-41, describes the design of a bipolar corona ionizer using a pair of sonic jet ionizers of different polarities. The ionizer is characterized in terms of ion output and particle generation for several electrodes, orifice plate materials, and ionizer operating conditions. The sonic jet ionizer appears to generate more particles than typical free corona ionizers. This might be due to a stronger and more reactive corona discharge. The use of silicon electrodes in the sonic jet ionizer resulted in unacceptable levels of particle formation. Lower particle generation could be achieved by using tungsten carbide electrodes and molybdenum orifice plates.

Patent publication U.S. Pat. No. 6,544,484, TSI Inc., 8 Apr. 2003, describes a system for analyzing aerosols. The system incorporates a corona discharge ion generator with a positively or negatively charged corona discharge needle formed of platinum or a platinum alloy. A high speed (40-210 meter per second) air flow sweeps the ions away from the corona discharge, and propels the ions into a mixing chamber in a turbulent jet that encounters an aerosol that is also provided to the mixing chamber. In one version of the ion generator, the ions are carried into the mixing chamber through an orifice formed in a positively or negatively biased plate. In another alternative, the aerosol droplets are electrostatically generated, and propelled into the mixing chamber as an aerosol jet that opposes the ion jet to enhance mixing of the charged droplets and the ions. In this version, the droplets are advantageously neutralized to leave predominantly singly charged positive and negative particles. The problem with this system is that the flow ratio of the aerosol to the clean air may change during the measurement, for example due to contamination of the filter. This form of mixing ionized air with the aerosol by opposed jets is difficult because the set-up is very sensitive to jet properties like jet direction and jet velocity, and thus the jets tend to be unstable. Ion losses is such set-up are very high, typically more than 99% and even higher than 99.9%

Patent publication U.S. Pat. No. 3,413,545, Regents of the University of Minnesota, 26 Nov. 1968, describes an electric aerosol particle-counting and size-distribution system for particles in the 0.01 to 2 micron size range. An aerosol chamber unit having a gas ionizing device and a diffusion chamber imparts a unipolar charge on aerosol particles in proportion to the size of the particles. The charged particles are delivered to a mobility analyzer having a housing with an elongated chamber. A particle-collecting electrode projects axially into the chamber above a current collector and a sensor filter connected to an electrometer. Collecting voltages up to 30 kV are used in the system. The mixing in the system is inefficient and thus the ion losses are probably very high, typically more than 99.9%.

Patent application US 2006/0144124 A1, Takeshi Kusaka, et al., 6 Jul. 2006, describes a soluble organic fraction, SOF, measuring system that can continuously measure SOF and a soot measuring system that can continuously measure soot. The two are connected by an exhaust gas line. The soot measuring system comprises a diluter that selectively dilutes either one of the exhaust gas and a standard gas whose hydrocarbon concentration is known with diluent gas, and extrudes it. A dilution ratio adjusting device can adjust a dilution ratio of the diluter. A soot detector continuously detects soot in the exhaust gas or the standard gas diluted by the diluter. The SOF measuring system can be connected with the diluter so that an exhaust gas analyzer can measure the hydrocarbon concentration in the standard gas diluted by the diluter. The publication does not mention charging the diluting air.

The problems with the prior art systems are: charger soiling, poor mixing of ionized air and aerosol, varying sample flow, and high ion losses. All these problems make the prior-art systems unstable, especially for on-line measurement of combustion engine exhaust gas particles. The current systems are also large and cannot be used in monitoring the particle emissions from diesel vehicles. The large mixing chamber in some prior-art systems also slows down the response time of the measurements.

SUMMARY OF THE INVENTION

The aim of the current invention is to introduce a process and an apparatus that solves the problems of the prior art.

The important components of the process and the apparatus are defined below.

'Ejector' is a device using a jet of gas 1, to withdraw gas 2 from a space. The flow of the jet of gas 1 is called the 'main flow' and the flow of the gas 2 is called the 'side flow'.

'Swirl' is a process to cause gas to move with a twisting or whirling motion.

'Ion trap' is a device that uses a combination of electric or magnetic fields or diffusion to capture ions in a region.

It is advantageous to combine the inventive solutions to solve several problems. Thus, soiling can be prevented by using a gas flow and the same gas can be used, when ionized, as the main flow of an ejector. Efficient mixing can be achieved by an ejector, and short mixing time can be achieved by using a high-velocity ionized gas flow for the ejector main flow. Such high-flow velocity and efficient mixing dramatically reduce ion losses. Rather than measuring the combustion engine exhaust particle emissions inside the exhaust duct, a constant sample flow is used, making the measurement process more stable. All solutions described in this invention make the measurement process more stable.

It is known that if swirling jets are used in opposed jet mixing, the end result is less stable than the result when using non-swirling jets. Thus, swirling jets are avoided in such systems, e.g. in the one described in U.S. Pat. No. 6,544,484 B1. The inventor has, however, surprisingly found that if swirling gas flow is used as the main flow in the ejector, the combined flow tends to be more stable. Thus, swirling main flow is advantageous for the invented process.

The process for monitoring the particle concentration in a gas uses efficient mixing in an ejector for solving the problems of the prior art systems. The main flow of the ejector consists of essentially clean ionized gas flow. The phrase 'essentially clean' means that the particle concentration in the ionized gas is so low that it does not adversely affect the monitoring process. The speed of the clean air is preferably sonic or close to sonic, but lower speeds can be utilized as well. The main flow creates suction in the side flow channel and thus educts a sample flow from the particle-containing gas and delivers the sample flow to the monitoring apparatus. The ionized clean gas forms the main flow and the sample flow forms the side flow. The main flow should advantageously be as small as possible. The inventor has surprisingly found that a reasonable suction pressure to the side flow channel can preferably be achieved with main flow to side flow ratio 1:1 and even more preferably with main flow to side flow ratio 1:3. The inventor has also surprisingly found that when an ejector is used as described in the invention, two different phenomena—efficient transfer of momentum and effective particle charging—happen in a single process step. This is advantageous in shortening the process time and thus reducing ion losses. This efficient mixing makes it possible to design small measurement apparatuses with fast response time, which is a great advantage when measuring vehicle emissions.

When the particle concentration of the gas is monitored, it is advantageous to produce a essentially constant gas flow through the measurement apparatus. Typically, the mass flow in the exhaust duct of a combustion engine is anything but constant, typically depending on engine rpm. Using an ejector for drawing the sample flow from the exhaust duct results an essentially constant side flow, the flow being typically pulse-free, i.e. constant. Such a flow can then be modulated or switched in a controlled way.

One of the problems with prior art technology is inefficient mixing of clean air and particle-containing gas. The inventor has found that an ejector is efficient in mixing the main flow and the side flow, especially when using a swirling main flow. In the ejector, the main and side flows are advantageously fed close to each other, which greatly improves mixing homogeneity and rate when compared to prior art systems. The instability problems existing with prior art systems are surprisingly avoided with the ejector. Surprisingly, it was also found that high gas velocity of the main flow and efficient mixing reduce ion losses, with ion losses prior to particle charging preferably less than 99% and more preferably less than 90%. As the ion losses are considerably lower than in prior art systems, the ionizer power supply can be smaller, providing an economic benefit. For efficient measurement, it may be advantageous to switch or modulate the main flow thus carrying out the measurement in AC-mode rather than in DC-mode. Another embodiment for realizing the AC-mode is to connect a chamber parallel to a constant gas flow and to change the volume of the chamber to create a pulsing flow.

Ions that are not attached to particles have to be removed after the mixing occurs. The ions are removed by an ion trap; the removal mechanism being either electrical or by magnetic field or diffusion (these mechanisms can also be combined). The nuclei-sized particles can also be trapped to the ion trap, if the trap voltage is increased to a suitable value, the absolute voltage depending, for example, on the geometry of the ion trap, gas flow speed, etc. The size of the trapped particles can be further increased by increasing the trap voltage. Thus it is possible to trap the particles using three different voltages that provide an indication of the size distribution of the accumulation-sized particles, which can be advantageously used in estimating the mass or number concentrations. Measuring the electrical current corresponding to different ion trap voltages allows the estimation of various parameters of the nuclei-sized particles and the accumulation-sized particles, like the particle concentration and the mean particle size. The ion trap voltage can be either switched or modulated between at least two different voltages.

Especially when monitoring hot gas flows, like exhaust gases of a combustion engine, the particle concentration may change in the measurement apparatus as the cooling gas generates nuclei-sized particles. As explained above, the ion trap can be adjusted to a high enough voltage to trap these nuclei-sized particles and thus the particles formed in the measurement apparatus itself do not adversely affect the measurement result. In some cases, however, it may be advantageous not to remove the nuclei-sized particles that are created in the measurement apparatus, as these nuclei-sized particles provide an indication of the particles created after the exhaust gases exit from the exhaust duct. The creation of such nuclei-sized particles can be increased by cooling the ejector main flow. Thus, ion trap voltage switching or modulation can be used for analyzing various parameters from the exhaust gas of a combustion engine.

A preferred embodiment for ionizing the clean gas is to use a corona discharger. The clean gas is advantageously fed with high speed from the close vicinity of the corona discharger so that the corona needle or equivalent is protected by the clean gas flow. The high-speed gas flow also increases ion production compared to a free-space corona discharging and decreases ion losses to the apparatus walls etc.

The electrical corona discharge may produce particles that disturb measurement when the particle concentration in the measured gas is low. This may be the case, for example, when the process is used to monitor particle concentrations before and after a particle trap in the exhaust duct of a diesel combustion engine. Such a measurement can provide an indication of the filtering capacity or maintenance need of the particle trap. In order to minimize particle production by the corona discharge, it is advantageous to manufacture the corona needle and the nozzle surrounding the corona needle from a refractory metal or metal alloy, such as tungsten, rhenium, tantalum, molybdenum, iridium, niobium, ruthenium, hafnium, zirconium, vanadium, chrome, alloy C-103, alloy KBI-3, nickel-chrome alloys, tungsten carbide or similar. It is also advantageous to use dry clean gas flow to minimize particle production in the corona discharge.

Clean gas ionization can also be achieved by sparking, thermal emission, surface charging or ionizing radiation.

Because the side flow of the measurement apparatus can be kept essentially constant, the measurement value can be processed with the value of the mass flow of the particle-containing gas and thus the emissions from a combustion engine can be calculated.

The electrical charge carried by the particles is monitored by measuring the electrical current escaping with the particles. This current measurement method is known from the prior art and with the current invention it provides a benefit by removing the need of capturing the charged particles.

In addition to a combustion engine monitoring, the present invention can be utilized in monitoring particles in ventilation systems, in industrial processes utilizing nanosized particles, and in personal particle measurement apparatuses.

BRIEF DESCRIPTION OF THE DRAWINGS

In the following, the invention will be described in more detail with reference to the appended principle drawing, in which.

For the sake of clarity, the figures only show the details necessary for understanding the invention. The structures and details that are not necessary for understanding the invention and that are obvious for a person skilled in the art have been omitted from the figures in order to emphasize the characteristics of the invention.

DETAILED DESCRIPTION OF PREFERRED EMBODIMENTS

Figure 5:
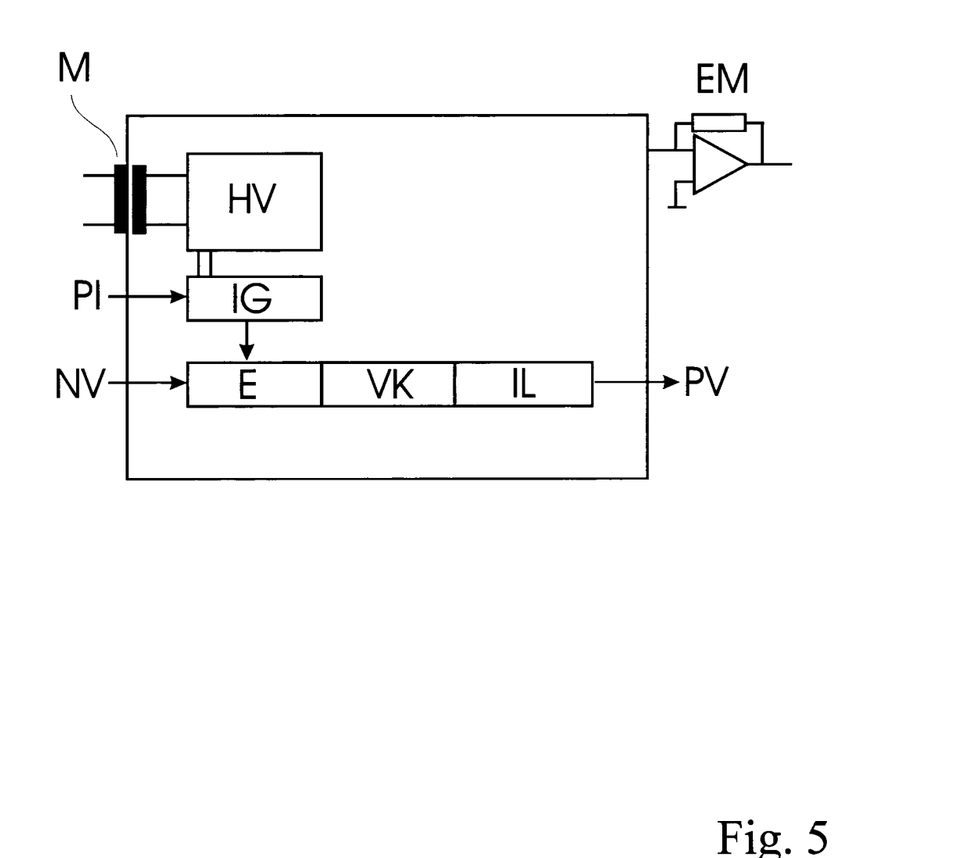
FIG. 5 shows the different functional modules of the process.

FIG. 5 shows the invented process as separated to different functional blocks. The sample flow NV is sucked from the duct or channel where the particle-containing gas flows via an ejector E. Pressurized air flow PI forms the main flow and an ionizer IG is used to ionize the pressurized air flow. The ionizer IG is preferably based on corona discharging, and the necessary high voltage for the corona discharge is provided by a high voltage source HV that is electrically isolated using a transformer M. The ionized air flow is mixed with the sample flow and the particles of the sample flow are charged in the charging chamber VK. It is to be understood that the charging chamber is really a functional block and the charging preferably takes place in the ejector essentially at the point where the main flow and the side flow meet each other. The ions that are not attached to particles are removed by the ion trap IL before the flow PV exits the measurement apparatus. The current exiting the measurement apparatus is measured by the electrometer EM.

Figure 1:
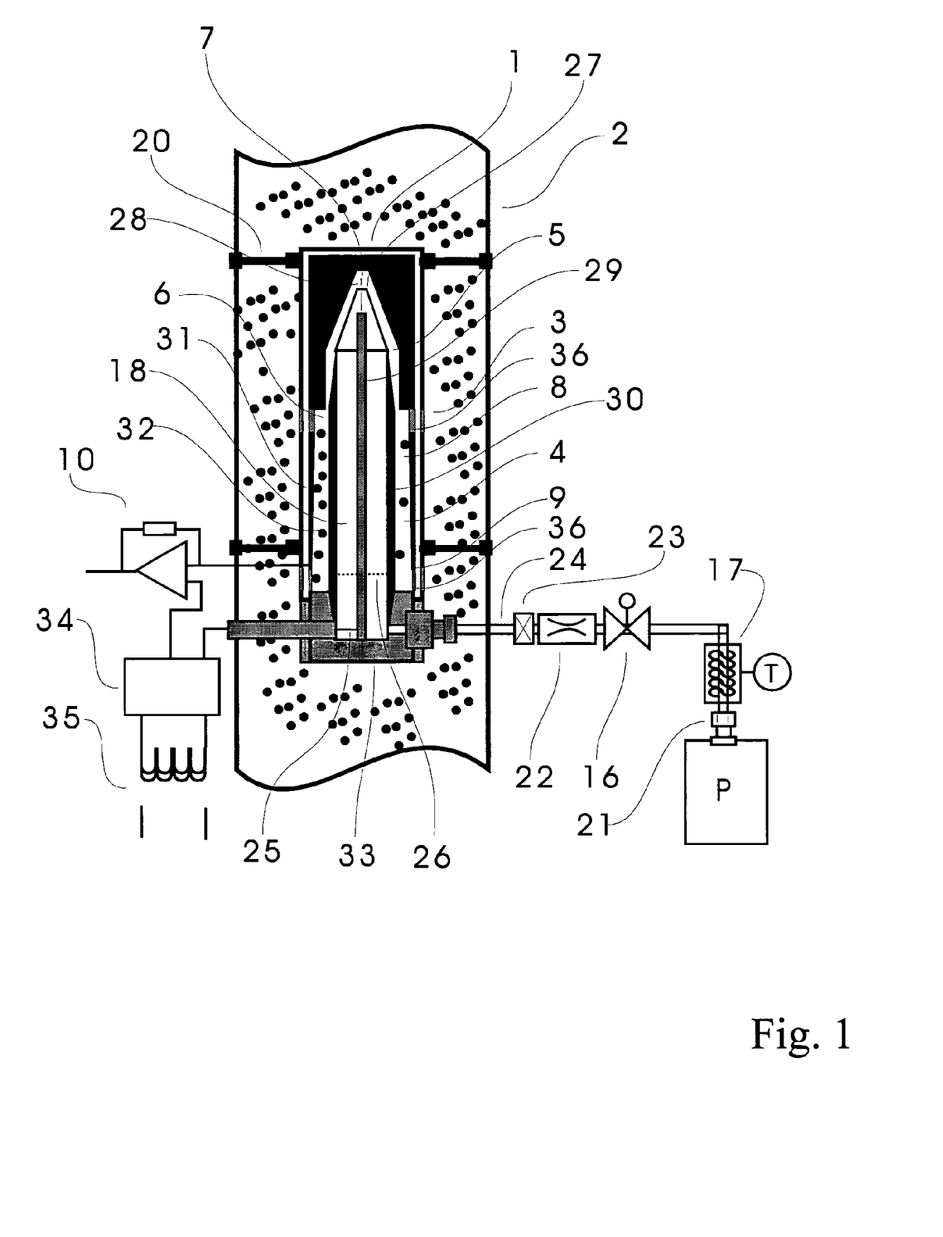
FIG. 1 shows an embodiment of an apparatus for monitoring the particle concentration in gas.

FIG. 1 shows an embodiment where the process is used to monitor the particle concentration from the exhaust duct of a combustion engine and the apparatus can be used to monitor the fine particle emissions from a diesel engine. The measurement apparatus 1 comprises a means 3 for directing the sample flow to the measurement channel 4, a means 5 for directing essentially clean, ionized gas to the measurement channel 4, a means 6 for mixing the clean gas flow and the sample flow, a means 7 for ionizing the clean gas, at least one charging chamber 8 for charging the particles, at least one ion trap 9, and at least one current measurement unit 10 for measuring the current carried by the particles. Additionally, the apparatus 1 comprises a means 16 for switching or modulating the essentially clean gas flow and a means 17 for regulating the temperature of the clean gas. FIG. 1 also shows a means 20 for connecting the apparatus 1 to the exhaust duct, a means 21 for connecting the apparatus to a pressurized air line, a pressurized air chamber, or a similar gas flow production unit. The embodiment also includes a means 22 for controlling the clean air flow, a means 23 for filtering the pressurized air and a means 24 for directing the pressurized air to the measurement apparatus 1.

The pressurized air is fed from the air source P to the temperature regulator 17, which can either heat or cool the air. The magnetic valve 16 is switched to feed the air to the flow controller 22, so that the flow can be set to a desired value. The flow controller 22 can be an adjustable valve, a critical aperture, a flowmeter, a mass flow controller, or a similar device. The flow controller 22 is connected to a filter 23, which essentially removes the particles from the pressurized air so that the particle concentration in the pressurized air is significantly lower than the particle concentration in the sample flow. The clean air is then fed to the measurement apparatus 1 through the connector 24. The pressurized air flows to the center channel 18 of the measurement apparatus and the flow may be stabilized with a restrictor plate 26. The center channel 18 may also be designed and constructed so that the flow will be forced to swirl, which is advantageous for various purposes as described above. The flow then exits through the nozzle 27. The ionization device 7 ionizes the gas exiting from the nozzle 27. The nozzle 27 is advantageously constructed so that the gas flow exits from near the corona needle 28. This helps the corona needle 28 to stay clean and improves ion production. High flow velocity in the nozzle 27 reduces ion losses. A high voltage is connected to the corona needle 28 via the electrode 29. The high voltage source 34 is electrically isolated from the rest of the system via the transformer 35 and an electrical insulator 33. Electrode 29 has the same electrical potential as the electrode shield 30. Obviously, the polarity of the corona needle and the counter electrode may be switched. The ionized gas flow is fed into the measurement channel 4. The sample flow from the duct 2 is also fed to the measurement channel 4 through the sampling means 3. The sampling means 3 is preferably the side flow channel 14 of the ejector 11 shown in FIG. 2. The ionized clean gas flow 13 forms the main flow of the ejector 11 and creates a suction in the side flow channel 14, the characteristics of the side flow depending essentially only on the geometry of the ejector 11 and the characteristics of the main flow. In a preferred embodiment, the ratio of the main flow to the side flow is small. The geometry and thus the behavior of the main flow 13 can be adjusted by, for example, varying the design of the electrode shield 30. The gas velocity or the electrical field intensity can be changed either locally or throughout the whole measurement channel. The ionized clean gas flow and the sample flow are mixed in the mixing section 6 of the measurement channel 4. The mixing section 6 should be understood as a functional block that may or may not be physically separated from the measurement channel 4. The mixing section 6 is designed so that the clean gas and the particle-containing gas are effectively mixed together in a minimum time. The flows can be set to swirling motion for effective and stable mixing. The particles are charged during the mixing and thus the ionization chamber 8 should also be considered a functional block; the mixing and the ionization may be overlapping functions. The ions not attached to particles are removed by the ion trap 9. Depending on the mechanical construction of the apparatus 1, such as the design of the electrode shield 30 and the design of the apparatus' outer wall 31, and depending, among other parameters, on the mass flow values and the voltage of the ion trap 9, the ion trap 9 may also be adjusted to trap nuclei-sized particles and even the smallest particles in the accumulation-sized range. A preferred embodiment is to adjust the ion trap voltage, using a higher voltage to trap larger particles. The actual voltage of the ion trap depends on the other design and gas flow parameters, but typically the ion trap voltage may be 1 to 30 kV.

The charge carried by the ionized particles 32 flowing through the measurement channel 4 can be measured by measuring the net current exiting from the ionization device 7. To measure small currents, typically at pA level, the ionization device 7 is electrically isolated from the rest of the system by the electrical insulator 33 and the isolating transformer 35. The electrometer 10 is assembled between the ionization device 7 and a point having a galvanic contact with the wall 31 of the measurement channel 4. One terminal of the high voltage source 34 is connected to the electrode of the ionization device 7 via a means 25 and the terminal is connected to the amplifier of the current measurement device 10. The other input of the electrometer 10 is connected to the wall 31 of the measurement channel 4, which also has a galvanic contact to the ion trap 9. With such setup, the electrometer 10 measures the charge escaping from the measurement channel via the ionized particles, and thus measures the escaping current.

The net-like electrodes 36 prevent free ions in the measurement channel 4 from escaping to the duct 2. In the preferred embodiment, the net-like electrodes 36 are connected to both flow apertures of the double-skinned measurement apparatus 1. The electrodes prevent ions from escaping even though the apertures on the electrodes are sufficiently large to allow the particles to flow through them. The net like electrodes 36 are not absolutely necessary in the apparatus 1 because ion escape can also be prevented, for example, by suitable gas flows.

Figure 2:
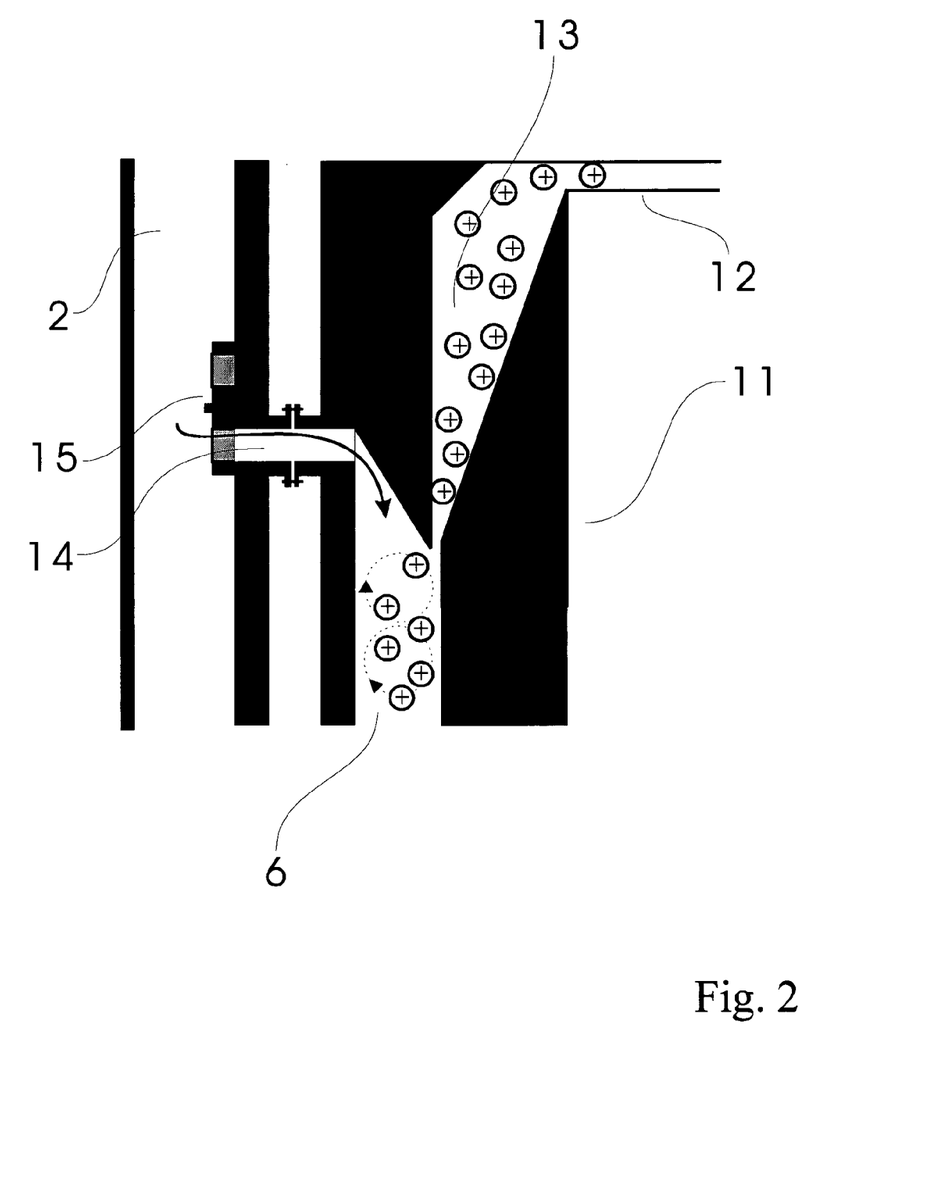
FIG. 2 shows a detail of the ejector.

The flow in the measurement channel 4 can be pulsed by switching or modulating the main flow of the ejector 11, for example by pulsing the magnetic valve 16. Such switching or modulation causes a similar switching or modulation of the side flow, enabling the total flow to be either switched or modulated in a well-controlled way. This control enables the electrometer 10 to work in a virtual AC-mode, which provides more reliable measurement than in a DC-mode. The sample flow may also be switched or modulated. FIG. 2 shows an embodiment where the sample flow may be modulated by a rotating disc 15 that covers the opening to the sample flow channel 14.

Figure 3:
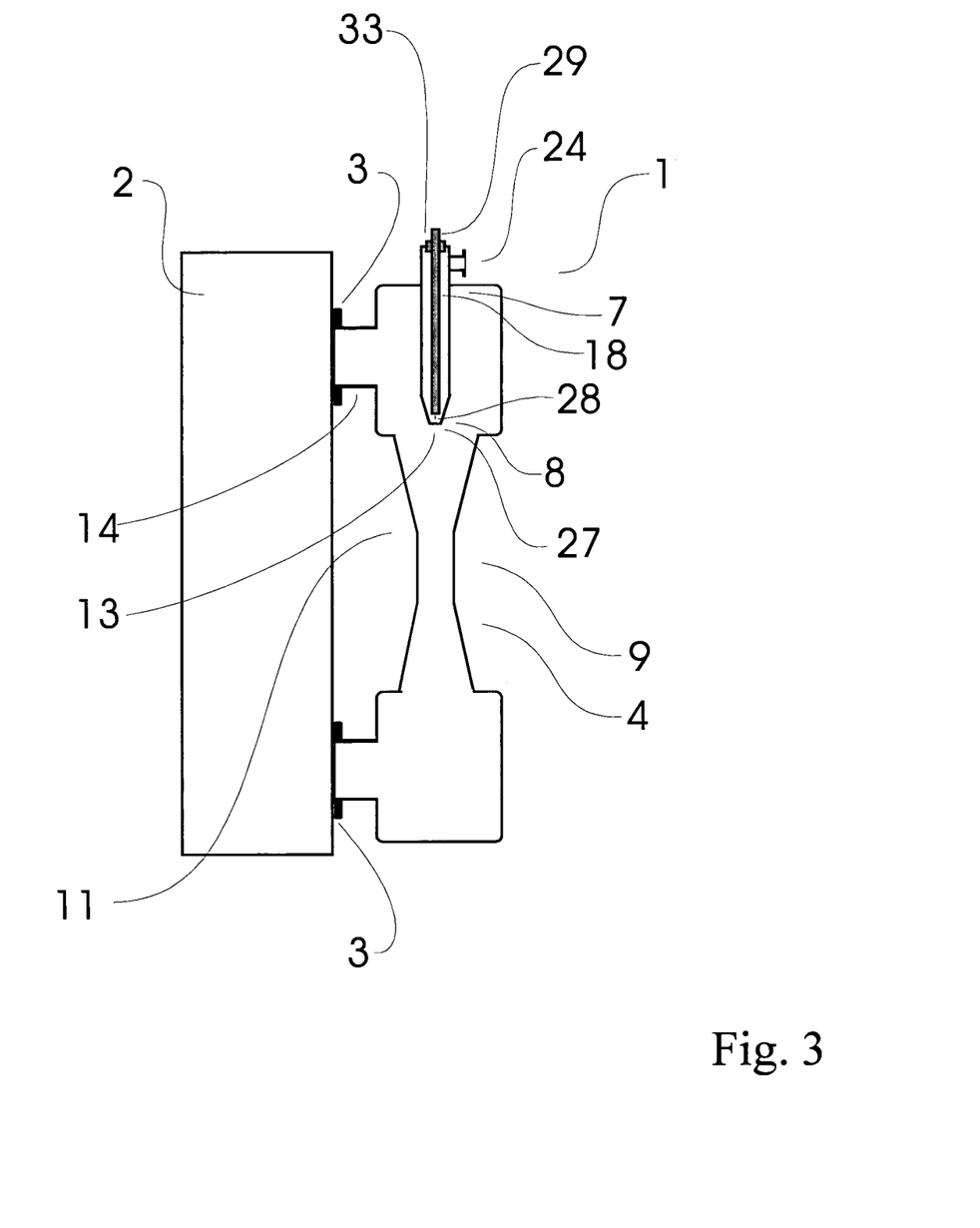
FIG. 3 shows an embodiment of an apparatus where the main flow and the side flow flow in the same direction.

FIG. 3 illustrates a way to organize the sample gas flow and the clean ionized gas flow in the invented apparatus. The ionizing device 7 uses a corona needle 28 to ionize the clean gas flow flowing in the center channel 18. Gas exits from the nozzle 27, which essentially forms the main channel 13 of the ejector 11. The main flow and the sample flow that is educted through channel 14 are effectively mixed in the mixing zone 8. The center channel 18 may be designed to swirl the gas, which further increases the mixing efficiency. Because the gas residence time in the ionizing device 7 is short and an efficient mixing is carried out in ejector 11, the ion losses in the apparatus are preferably less than 99%, more preferably less than 90%, and most preferably less than 80%. This is a considerably improvement over prior art systems, providing great economic benefits, for example, in reducing power supply requirements.

Figures 4, 4B:
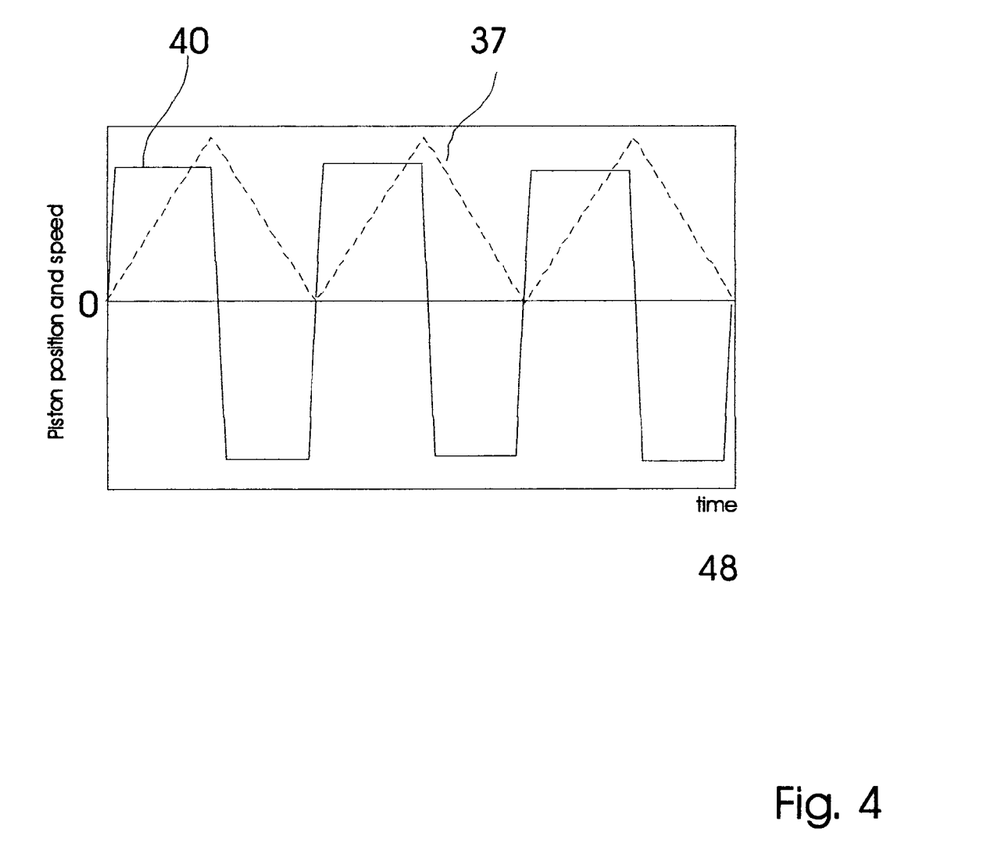
FIG. 4 shows an embodiment of an apparatus for modulating the clean air flow.
Figure 4A:
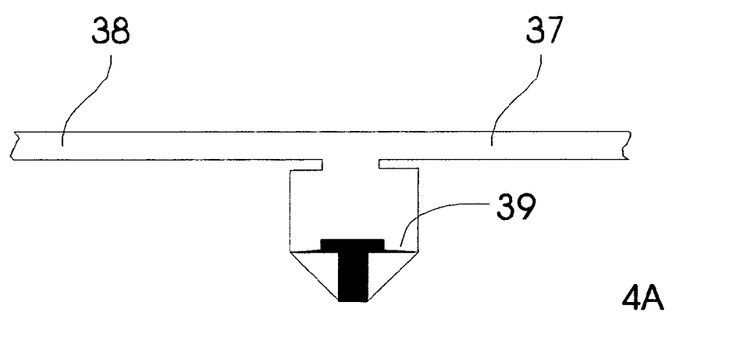

FIG. 4 illustrates an embodiment where the gas flow modulation is carried out by connecting a variable-volume chamber in parallel with the constant clean air flow. An essential part of this structure is a piston or a diaphragm 39 whose movement or position can be varied within a certain range. FIG. 4a shows the construction in principle while FIG. 4b shows the formation of a cycling flow 37 as a sum function of the constant flow 38 combined with the effects of the moving piston 39. The figure shows the modulation of the piston as a square-wave; the amplitude of the modulation is set so that the minimum value of the cycling flow is zero. Obviously, the wave form or the flow amplitude may differ in various ways. In another embodiment, the moving part may be a diaphragm similar to an audio element. This simple structure has the advantage of being essentially maintenance-free and the coil 38 can generate a wide range of wave forms. Obviously, the reciprocating piston 39 can be constructed in various ways.

It is obvious for a person skilled in the art that a tight purity requirement is required for the electrical insulators, especially for ones whose leaking currents would add to the current signal being measured. In hot environment, like in the exhaust duct of a combustion engine, the electrical insulation capability of an insulator is reduced. Due to the low current values used in these settings, the measurement electronics needs to be positioned near the measurement electrodes, where the hot temperatures of the system also increase the temperature of the measurement electronics. This increases the noise of the measurement electronics. In one embodiment of the current invention, these problems are solved by taking the same gas flow that is used to prevent the insulators from soiling and overheating and using it to also cool the measurement electronics.

It is possible to produce various embodiments of the invention in accordance with the spirit of the invention. Therefore, the above-presented example must not be interpreted as restrictive to the invention. Instead, the scope of the invention is set out in by the claims below.

The invention claimed is:

1. A process that is used for monitoring the concentration of particles in a particle-containing gas, and includes the steps of:
   providing a main flow of essentially particle-free gas;
   ionizing the main flow;
   using the main flow to educt a sample flow from the particle-containing gas;
   mixing an essential part of the sample flow with an essential part of the main flow and thereby charging at least a fraction of the particles that were in the sample flow;
   measuring an electrical charge that is carried by charged particles that are escaping from the system; and
   using the measured charge of the particles that are escaping from the system to estimate the concentration of particles in the original particle-containing gas.

2. The process of claim 1 wherein the main flow to sample flow ratio is less than 1:1.

3. The process of claim 1 wherein the main flow to sample flow ratio is less than 1:3.

4. The process of claim 1, wherein ion losses prior to particle charging are less than 99%.

5. The process of claim 1, wherein ion losses prior to particle charging are less than 90%.

6. The process of claim 1, wherein, after the essential part of the sample flow and the essential part of the main flow are mixed, ions that are not attached to any particle are removed by an ion trap.

7. The process of claim 1, wherein the main flow is switched or modulated.

8. The process of claim 6, wherein the ion trap also traps nuclei-sized particles.

9. The process of claim 8, wherein the nuclei-sized particles are removed by increasing the voltage of the ion trap.

10. The process as in claim 6, wherein
   a. the voltage of the ion trap is switched or modulated between at least two different values; and
   b. the currents corresponding to the at least two different values are used to calculate the concentration of nuclei-sized particles or the concentration of accumulation-sized particles or the mass concentration or the volume concentration or the size distribution or the concentration of particles created after exhaust gasses exit an exhaust duct, or any combination thereof.

11. The process as in claim 1, comprising using a measurement signal that correlates a total flow of the particle-containing gas and the particle concentration of the sample flow to calculate the particle concentration in the particle-containing gas.

12. The process as in claim 1, wherein the essentially particle free gas is ionized by corona discharge.

13. The process as in claim 1, wherein the process is used for particle monitoring before and after a particle trap.

14. An apparatus for monitoring particles in a duct or channel, comprising:
   a. means for ionizing essentially particle-free gas;
   b. at least one eductor that draws a sample flow from a particle-laden gas in the duct or channel;
   c. means for feeding essentially particle-free, ionized gas to the main flow channel of the eductor;
   d. means for mixing the essentially particle-free, ionized gas and the sample flow from the particle-laden gas; and
   e. means for measuring the charge of particles that are escaping from the system and using that measurement to estimate the concentration of particles in the duct or channel.

15. The apparatus of claim 14, wherein the ion losses that occur before the essentially particle-free gas arrives at the means for mixing are less than 99%.

16. The apparatus of claim 14, comprising an ion trap.

17. The apparatus of claim 16, comprising means for switching or modulating the ion trap voltage at least between two different values.

18. The apparatus as in claim 14, comprising means for switching or modulating the essentially particle-free ionized gas flow.

19. The apparatus as in claim 14, comprising means for controlling the temperature of the essentially particle-free ionized gas flow.

20. The apparatus as in claim 14, comprising a corona discharger for ionizing the essentially particle-free gas.

21. The apparatus as in claim 20, comprising means for directing the essentially particle-free gas flow to the vicinity of the corona discharger.

22. The apparatus as in claim 14, wherein the means for feeding essentially particle-free, ionized gas is electrically isolated from the rest of the system, and at least one charge-measuring means is arranged to determine a net charge of the emitted particles by measuring a discharging current carried by those particles, which discharging current is measured between the means for feeding essentially particle-free, ionized gas and a point in a galvanic contact with a flow channel wall of the apparatus.

23. The apparatus as in claim 14, comprising means for providing a gas flow that cools the means for ionizing and components related to the means for ionizing.

24. The apparatus of claim 14, wherein the ion losses that occur before the essentially particle-free gas arrives at the means for mixing are less than 90%.

* * * * *